United States Patent [19]

Mathews et al.

[11] Patent Number: 4,814,351

[45] Date of Patent: Mar. 21, 1989

[54] SCALP TREATMENT

[75] Inventors: Roger A. Mathews, Newbury Park; David W. Cannell, Los Angeles, both of Calif.

[73] Assignee: Redken Laboratories, Inc., Canoga Park, Calif.

[21] Appl. No.: 67,632

[22] Filed: Jun. 26, 1987

[51] Int. Cl.$^4$ ............................................. A61K 31/195
[52] U.S. Cl. ..................................... 514/566; 514/880; 514/881
[58] Field of Search ......................... 514/566, 880, 881

[56] References Cited

U.S. PATENT DOCUMENTS

| | | | |
|---|---|---|---|
| 2,604,401 | 7/1952 | Ely | 99/4 |
| 2,875,129 | 2/1959 | Bersworth et al. | 167/55 |
| 3,838,196 | 9/1974 | Mercer et al. | 124/319 |
| 3,932,655 | 1/1976 | Conn | 424/317 |
| 3,984,535 | 10/1976 | Ghilardi et al. | 424/47 |
| 4,195,095 | 3/1980 | Sheffner | 424/317 |

OTHER PUBLICATIONS

Conn's, *Current Therapy*, pp. 599–603 (1984).
Conn's, *Current Therapy*, p. 662 (1981).
Chem. Abst. 101:157470e (1984), (Derwent Abstract No. 84-177754/29).
Chem. Abst. 96:214340s (1982).
Chem. Abst. 72:53675s (1970).
Chem. Abst. 66:5706z (1967).

*Primary Examiner*—Douglas W. Robinson
*Assistant Examiner*—Joseph A. Lipovsky
*Attorney, Agent, or Firm*—Christie, Parker & Hale

[57] ABSTRACT

A scalp treatment for reducing average daily hair loss periodically applies to the scalp a composition containing an active chelating agent sufficient to chelate at least 0.3 milligrams of divalent calcium ion per milliliter of the composition and leaving the chelating agent in contact with the scalp for at least eight hours. Particularly preferred chelating agents comprise ethylene diamine tetraacetic acid, citric acid, and soluble salts thereof.

11 Claims, No Drawings

4,814,351

SCALP TREATMENT

BACKGROUND OF THE INVENTION

This invention concerns a scalp treatment shown to decrease average daily hair loss in a number of people in statistically significant tests. An overall decrease of 21 percent of average daily hair loss has been shown after two months of treatment of a test panel. Average daily hair loss decreased for over 75 percent of the panelists. Statistically, there is a more than 90 percent confidence level that a decrease in average daily hair loss occurred in the test group as a whole.

There is no present evidence that the technique stimulates hair growth, and no tests for this effect have been made. No claims are made that this treatment affects "male pattern" baldness, and no tests have been made for such an effect. No tests have been conducted for abnormal hair conditions.

The whole topic of hair growth connotes elements of folklore, superstition, and even "quackery." Still a large number of valid scientific studies on hair growth or hair loss exist.

Falling hair has been approached in many different ways throughout history. Records from Egyptian tombs relate cures for baldness dating from the Bronze Age. Fats of the snake, hippopotamus, and other animals were regarded as topical treatments for hair loss. Since that remote period, little has changed until recently.

Modern approaches to the problem of hair loss have stressed several possible avenues of treatment.

The nutrient/microcirculation approach centers on supplying alleged nutritional factors or oxygen that the hair follicles may be lacking. No research to date has given evidence to support the concept that hair follicles senesce and fall in response to a vital nutrient or oxygen which becomes limiting. Similarly, treatment of falling hair by supplying nutrients has not been shown to have any effect.

A second approach has stressed "unplugging" of the hair follicle. This view suggests that the hair follicle is "strangled" by buildup of sebaceous secretions in the pilary canal. Treatment of this imaginary microscopic strangulation with products containing polyoxyethylene sorbitan fatty acid esters, such as polysorbate-60 or polysorbate-80, has gained some underground popularity, but again there is no scientific evidence of benefit.

Interest in hair loss and in hair growth has recently been rekindled by the promise of topically applied drugs (minoxidil, diazoxide, or viprostal, for example) which in some cases support hair regrowth in balding persons. The mechanism of actions of these drugs is not known and their safety and effectiveness are under study.

Human hair grows in cyclic fashion with each of the individual hair follicles responding independently to the physiological condition of the person. At any given time some 85 to 90 percent of the human scalp hair follicles are in the active stage of growth known as "anagen." This anagen state is characterized by active production of cells which keratinize to form the growing hair shaft. The growth of any individual hair follicle may proceed continuously for a variable period of up to six years. For reasons which are not fully understood, the anagen follicle passes into a state of metabolic quiescence (catagen) and then into a state of senesence (telogen) characterized by deterioration of the bulb and eventual loss of the structure, including the hair shaft. Under normal conditions the "germ" of the new anagen bulb is left behind by the extruded follicle so that a new bulb will differentiate and grow at virtually the same location as its predecessor.

When the cyclic nature of this process becomes unbalanced, that is, when generation of new anagen bulbs is retarded with respect to the entry of bulbs into catagen and telogen states, hair loss occurs. Balding, therefore, is the result of many cycles of hair growth out of balance, which is characterized by gradual diminution of the number of anagen bulbs over successive cycles. It is reasonable to assume that if hair follicles can be maintained in the active anagen state for a longer period, there will be less hair loss as follicles pass to the catagen and telogen states. The fewer bulbs lost in the normal progression of hair follicles or senescence, the fewer new bulbs need to take their place.

It is therefore desirable to provide a treatment which modulates the normal rate of conversion of active anagen bulbs to quiescent or senescent ones. It is desirable that such a treatment decrease the rate of shedding of hair. It is desirable that such a treatment maintain the anagen phase of bulb activity. It is desirable that such a treatment employ inexpensive, harmless materials and be performed by individuals without professional assistance.

SUMMARY OF THE INVENTION

There is, therefore, provided in practice of this invention according to a presently preferred embodiment, a topical scalp treatment which decreases the average daily hair loss in many individuals susceptible to such loss. Such a treatment comprises distributing onto the scalp a composition containing a sufficient amount of active chelating agent to chelate at least 0.3 mg of divalent calcium per milliliter of the composition and leaving the composition in contact with the scalp for at least eight hours. Preferably initial treatments distribute the composition onto the scalp at least daily. After a period of initial treatment, the frequency of application may be reduced to alternate days.

DESCRIPTION

Histochemical studies of hair follicles strongly indicate that anagen follicles differ from catagen and telogen follicles with respect to presence of calcium ions. Anagen follicles stain very sparingly for calcium, while catagen and telogen bulbs stain strongly for the ion. Vellus follicles react still more strongly to the stain. Vellus refers to the diminutive, nongrowing, nonpigmented, incompletely keratinized hair characteristic of the bald scalp. This is the common "peach fuzz" appearance of the scalp on bald persons.

Somewhat more quantitatively, it appears that the average calcium content of anagen bulbs is in the order of one nanogram per bulb. The average calcium content of catagen bulbs appears to be about twice as high. The calcium content of telogen bulbs appears to average about 4 nanograms per bulb, although some bulbs have shown calcium contents as high as 20 nanograms per bulb.

We believe that there is a progressive interaction of calcium ions with hair bulbs which produces gradual declining cell activity. When some threshold calcium concentration is present, the follicle activity shifts toward dormancy, and eventual loss of the follicle and attached hair shaft. In other words, we believe that calcium ion is a causative factor in progression of hair follicles from anagen to catagen to telogen states, rather than simply being an indicator or consequence of such progression.

Although not being bound by theory, we believe that during the active phase of growth, the hair follicle is "protected" from divalent calcium ion by virtue of a high content of strongly anionic sulfated mucopolysaccharides (SMPS) in the vicinity of the bulbs. Thus, an anionic gradient of calcium is created in which the divalent calcium ion is largely held away from the bulb by the anionic SMPS.

Accompanying the shift of follicles to dormancy is a precipitous decline in SMPS in the vicinity of the bulbs, which we believe allows the calcium ion gradient to approach the bulb, and may precipitate its senescence.

It is known that the roll of calcium ions in molecular biology is central. Calcium ion is involved in virtually every regulatory process. At low concentrations divalent calcium ion is essential for the growth of cells, but at high concentrations it becomes inhibitory. Calcium ions are central to the mechanisms of hormone-cell interactions, neurotransmission, muscle contraction, cell-cell adhesions, cell membrane fluidity, gene activation, and many other biological processes. Indeed calcium ion is a central regulating factor in terms of minute ionic fluxes which are "sensed" by cells and direct the triggering of various responses. It is reasonable to assume that calcium ion also plays a regulatory role in the health and activity of hair follicles.

We therefore theorize that inhibiting the interaction of calcium with hair follicles may reduce the rate of senescence and reduce hair loss. We therefore provide a topically applied product which contains material that can bind, chelate, sequester, or otherwise interact with and prevent the progressive ionic attack of calcium on hair follicles. Delaying the progressive influence of calcium on the hair bulbs may spare some of them from early passage to the telogen state, and prolong the period of active hair growth.

A composition employed in practice of this invention comprises at least one active ingredient consisting essentially of active chelating agent. An ability to chelate at least 0.3 milligrams of divalent calcium per milliliter of composition is preferred. Such a composition is distributed on the scalp and left in place at least eight hours. Preferably such an application of the composition is made daily for at least the first month of treatment.

A preferred active ingredient is ethylene-diaminetetraacetic acid (EDTA) or soluble salts thereof, such as the sodium salt. Another desirable chelating agent is citric acid or soluble salts thereof. Other suitable chelating agents include glutamic acid, aspartic acid, lactic acid, glycine, and soluble salts and derivatives thereof such as, for example, dimethylglycine. Other difunctional carboxylic acids may also be used. It is preferred to use such materials as compared with possibly toxic, strong chelating agents such as oxalic acid. EDTA is probably the most powerful nontoxic chelating agent for calcium, and is therefore particularly preferred.

In such a composition, the concentration of active EDTA or equivalent calcium chelating agent is in the range of from 0.1 to 1 percent by weight. Preferably the concentration of EDTA is in the range of from 0.2 to 0.3 percent by weight. In addition to disodium EDTA or as a substitute therefor, the composition may comprise up to about 5 percent by weight of citric acid or glutamic acid. An exemplary composition comprises 0.1 percent by weight sodium glutamate in addition to 0.2 percent by weight disodium EDTA.

These proportions appear sufficient to provide the desired result without surplus concentration of the moderately expensive ingredients. It appears that these concentrations are appropriate for obtaining the desired result in a reasonably short period although a somewhat lower concentration may be satisfactory for a "maintenance" treatment.

It is particularly preferred that the active chelating agent for divalent calcium ion be present in the composition in a concentration sufficient to chelate at least 0.3 milligrams of calcium per milliliter of solution. This assures that there is adequate active chelating concentration on the scalp after carriers such as water and/or alcohol have evaporated. Preferably the concentration of EDTA or equivalent is no more than one sufficient to chelate about 1.5 milligrams of calcium per milliliter of solution. Higher concentrations result in insufficient spreading of the composition over the scalp on application and may result in nonuniform concentrations in areas that are inadequately wetted.

The chelating agent in the composition is active, that is, it has not already reacted with polyvalent ions such as iron or calcium in the water or other vehicle used with the active ingredient. EDTA and the like are sometimes used in hair treatment compositions made with tap water to avoid discoloration due to iron in hard water and similar effects. The amount of EDTA in the composition is typically slightly more than needed to sequester the iron, calcium and the like in the tap water, and little active chelating agent remains.

It is preferred that the composition for application to the scalp comprise as a vehicle a somewhat viscous liquid for ease of application to the scalp and avoidance of waste. Surfactants, preservatives, hair conditioners and the like may be included in such a composition. The vehicle should be safe enough for application to the scalp for non-volatile components to remain in place on the scalp for at least eight hours, and preferably substantially continuously.

The treatment comprises applying a composition containing the active chelating agent to the scalp at least daily during an initial month of treatment. Thereafter, treatment may be maintained by application of the composition on alternate days. An exemplary regimen is to apply the composition to the scalp before retiring to leave the active chelating agent in contact with the skin for about eight hours. It is also appropriate to apply the composition after shampooing to permit it to remain in contact with the scalp throughout the day. Strict adherence to such a schedule of application is not mandatory and occasional days of application of the composition to the scalp may be missed without detrimental results. For example, application of the composition to the scalp five or six days a week appears equivalent to application on a daily basis during the first month of treatment.

A suitable mode of application of the composition to the scalp is by way of droplets applied directly to the scalp in seprrated locations sufficient to cover the entire scalp. Preferably from five to seven milliliters of solution are applied. When applied as a liquid composition, flow can be expected to spread such droplets along the scalp so that the entire desired area is wetted. Such flow can be promoted by gentle massaging or rubbing with the finger tips.

In an exemplary embodiment, a viscous liquid composition containing the active calcium chelating agent may be packaged in small, relatively hard plastic bottles. A bottle holding about 60 ml. is conveniently manipulated and contains sufficient solution for about one week of treatment. Such a bottle is fitted with a tubular applicator cap having a small orifice at the end of the tube to contact the scalp. Simply touching the tip of the applicator to the scalp may result in sufficient liquid being placed on the scalp. The amount of liquid can be augmented by simply squeezing the bottle to extrude a droplet of liquid. Such droplets are applied directly to the scalp in scattered areas over the entire head and preferably gently rubbed to assure complete coverage. Some wetting of the hair inevitably occurs during such application.

The carrier for the active calcium chelating agent comprises deionized water, alcohol such as SD-40, or mixtures thereof. Water is preferred since it is inexpensive, and it is preferred to employ a slightly viscous liquid rather than the fluid "tonics" more commonly associated with alcohol-containing compositions. Alcohol may be included in the composition to expedite drying if desired.

Since the composition is applied to the scalp and left in place, it is desirable to include conditioners and the like which are separately beneficial to the hair and/or scalp. It is desirable to include surfactants in the composition for stabilizing the solution, for viscosity, and for promoting thorough wetting of the scalp. It is desirable to include preservatives for inhibiting growth of microorganisms.

It is preferred that the pH of the composition be in the range of from 4 to 7, and preferably in the range of from 5 to 5.5. This is a suitable pH for a composition to be left in contact with the skin and hair as provided in practice of this invention. Generally speaking, the materials employed in the composition are acidic in nature, and the pH may be adjusted to the desired range by additions of sodium hydroxide.

Thus an exemplary composition comprises the active calcium chelating agent, up to about 3 percent by weight surfactant, up to about 3 percent by weight conditioners for the hair and scalp, sufficient preservatives to inhibit growth of microorganisms, fragrance, and materials for increasing viscosity such as glycerin and sodium chloride.

An exemplary composition is largely water containing 0.2 percent by weight EDTA and 0.1 percent by weight glutamic acid, both in the form of the sodium salt. Such a composition may include conditioners such as Polyquaternium-11 or equivalent, up to about 2.5 percent by weight. An exemplary composition comprises 2 percent by weight Polyquaternium-11. This and similar quaternary ammonium salts also act as preservatives.

Such a composition may include up to about 2 percent by weight diethanolamine-oleth-3-phosphate. An exemplary composition comprises 1 percent by weight DEA-oleth-3-phosphate.

Such a composition may include up to about 1 percent by weight of polysorbate 80 or Tween 80. An exemplary composition comprises 0.5 percent by weight of such a surfactant.

Such a composition may include up to about 1 percent by weight octoxynol-9 or Triton X-100, a surfactant particularly suitable for stabilizing fragrance additives in the composition. Typically such a material is present at about 4 to 6 times the proportion of fragrance to provide such stabilization. For example, such a composition having 0.05 percent by weight fragrance oils has 0.2 percent by weight of octoxynol-9.

A mixture of such surfactants is employed in practice of this invention for stabilization of a mixture of conditioners, fragrances, and the like.

A desirable conditioner employed in practice of this invention comprises up to about 0.3 percent by weight of allantoin acetyl methionine. An exemplary composition comprises 0.2 percent by weight of this conditioner for the scalp. This material has a particularly soothing and healing characteristic.

The composition may comprise up to about 0.5 percent by weight of panthenol. An exemplary composition comprises 0.1 percent by weight panthenol as a conditioner.

The composition may comprise up to about 0.1 percent by weight of live yeast cell derivative. It is believed that such live yeast cell derivative evolves oxygen and may oxygenate tissue as well as condition the hair. Another conditioner employed in practice of this invention may be up to about 0.5 percent by weight of zinc protein complex. An exemplary composition comprises 0.15 percent by weight of zinc protein complex. The presence of the zinc may inhibit dandruff. Such live yeast cell derivative and zinc protein complex are available from Brooks Industries, South Plainfield, N.J.

Another suitable ingredient in the composition comprises up to about 0.2 percent by weight of tocopheryl-nicotinate. An exemplary composition comprises 0.1 percent tocopheryl-nicotinate. Such material is a vitamin E derivative and a mild irritant which may stimulate hair growth. The material is available from BASF Incorporated, New York, N.Y. Other hair growth stimulants may be included.

A complex of preservatives is desirable in the composition since the surfactants and conditioners provide considerable nutrition for microorganism contamination. Thus, for example, the composition may comprise up to about 0.5 percent by weight methylparaben and up to about 0.5 percent by weight diazolidinyl urea. An exemplary composition comprises 0.25 percent methylparaben and 0.3 percent by weight diazolidinyl urea. It is also desirable to include up to about 0.4 percent by weight of sorbic acid for inhibition of molds. An exemplary composition comprises 0.001 percent sorbic acid.

It may also be desirable to include sodium chloride or glycerin for increasing viscosity for the composition. For example, up to about 1 percent by weight of glycerin may be added.

Over the last few years we have conducted various studies of calcium in hair bulbs and efficacy of treatment involving applying an active chelating agent for divalent calcium to the scalp. In an exemplary study conducted with a panel of 14 volunteers who completed the test regimen, there was an overall decrease of 21 percent in average daily hair loss after two months of treatment, and 78 percent of the panelists showed a decrease.

In this test an exemplary composition had as its active chelating agent 0.2 percent by weight disodium EDTA and 0.1 percent by weight sodium glutamate. The composition also comprised 2 percent by weight polyquaternium-11 one percent by weight DEA-oleth-3-phosphate, 0.5 percent by weight polysorbate 80, 0.2 percent by weight octoxynol-9, 0.2 percent by weight allantoin acetyl methionine, 0.1 percent by weight panthenol, 0.015 percent by weight live yeast cell derivative, 0.15 percent by weight zinc protein complex, and 0.1 percent by weight tocopheryl-nicotonate. As preservatives the composition comprised 0.25 percent by weight methylparaben, 0.3 percent by weight diazolidinyl urea, and 0.001 percent by weight sorbic acid. The composition also comprised 0.001 percent by weight glycerin and 0.05 by weight fragrance oils. The balance of the composition was deionized water.

The test panel, comprising seven men and seven women who completed the three-month test regimen, ranged in age from about 20 to 55 years old. There was one black, two hispanic, two orientals, and the balance caucasians.

Each panelist was issued the same type of hairbrush and received a hairbrushing demonstration. Each panelist was requested to brush his or her hair the first thing upon arising in the morning before other grooming. The hairbrushing comprised approximately ten vigorous strokes over the entire head from front to back, ten strokes from back to front, and ten strokes from each side to the opposite side. Brushing was over a towel or other light cloth to collect any hairs that fell. In addition, all of the hairs in the brush were removed with tweezers. The total number of hairs collected each day were counted and saved in identified dated envelopes. The panelists were requested to continue their routine hair shampooing and grooming techniques and compositions with the only change being superimposing of the brushing and treatment according to practice of this invention.

During the first month the panel did only the standard brushing, and collecting and counting the hairs lost to provide a base for comparison. For the second and third months, the scalp was treared by adding the test composition.

The test composition was provided in a two-ounce (60 milliliter) bottle having a tubular applicator tip with a small orifice. Drops of liquic were applied to the scalp and gently rubbed around to wet the entire scalp. On average, about 5 to 7 ml of test solution was used per application. The test solurion was added in the evening before retiring for the night. There were a very small number of days when either the treatment or brushing was missed by a panelist, but the number of missed days is small enough that there should be no effect on the results.

The number of hairs collected by each panelist was averaged for each month of the test. The following table sets forth the number of hairs collected from each panelist for each of the three months. In this table "Month 0" refers to the base period prior to treatment. Months 1 and 2 refer to the first and second months of treatment.

| AVERAGE DAILY HAIR LOSS PER SUBJECT | | | | | | | | | | | | | | |
|---|---|---|---|---|---|---|---|---|---|---|---|---|---|---|
| Month | A | B | C | D | E | F | G | H | I* | J | K | L | M | N |
| 0 | 42 | 16 | 34 | 36 | 23 | 9 | 47 | 36 | 86 | 35 | 40 | 75 | 123 | 71 |
| 1 | 44 | 16 | 28 | 21 | 23 | 4 | 40 | 24 | 70 | 30 | 35 | 82 | 70 | 59 |
| 2 | 45 | 11 | 22 | 23 | 20 | 3 | 33 | 26 | 100 | 30 | 29 | 86 | 65 | 56 |

*Test panelist "I" was a man who appeared emaciated and developed anemia in the second month of the test. This condition may have contributed to the increase in hair loss as compared with the first month, which showed a decrease from the base. The actual influence of this condition was not determined, and the results were retained in the survey.

*Test panelist "I" was a man who appeared emaciated and developed anemia in the second month of the test. This condition may have contributed to the increase in hair loss as compared with the first month, which showed a decrease from the base. The actual influence of this condition was not determined, and the results were retained in the survey.

The results were analyzed by the standard student T-test. During the course of each month's collections, the numbers of hairs collected daily deviated from the mean by about plus or minus 20 percent. The data show that after one month of product use, the average daily hair loss decreased in 10 of the 14 panelists, as compared with the base month without treatment. Similarly, after two months of treatment, the average daily hair loss decreased in 11 of the 14 panelists, as compared with the base, that is, in 78 percent of the panelists.

Statistically, there is a 90 percent confidence level that there was a decrease in average daily hair loss for the group as a whole. There is not a 90 percent confidence level that there was a decrease in average daily hair loss for men in the group. However, if test panelist "I" is excluded, there is a 90 percent confidence level that there was a decrease in average daily hair loss due to the treatment. For women, there is a 90 percent confidence level that the treatment resulted in a decrease in average daily hair loss. When considering only the third month of the test, that is, the second month of treatment, there is a 99 percent confidence level that the treatment resulted in a decrease in average daily hair loss by women in the group.

When the data are divided into groups of those under 40 years of age and those over 40 there is a confidence level of more than 95 percent and less than 99 percent that there was a decrease in average daily hair loss in the second month of treatment for those panelists over 40. There was a 99.9 percent confidence level that there was a decrease in average daily hair loss for individuals under 40.

For the men as a group, there was an 11 percent decrease in average daily hair loss in the second month of treatment as compared with the base. Similarly, there was a 30 percent decrease in average daily hair loss for women as a group. For persons over 40 there was a 12 percent decrease in average daily hair loss. For person's under 40 there was a 25 percent decrease in average daily hair loss.

Analysis of hair bulbs retrieved from hairs collected during the test show an average calcium content in bulbs collected during the second month of treatment about one-half of the calcium content of bulbs collected during the month before treatment commenced. Thus, not only was there a decrease in average daily hair oss due to treatment, but also tne calcium content of hair follicles on the hair lost decreased about 50 percent, thereby suggesting that the active calcium chelating agent was actually reducing calcium content of the bulbs or inhibiting increase of calcium concentration in hair bulbs which would otherwise occur.

It might be noted that the chelating capacity of the active chelating agent in the composition increases with pH. Thus, although it is desirable to increase pH to enhance the chelating capacity, it is also desirable to maintain an acidic pH for best compatibility with the skin and hair for a "leave in" product which remains in contact with the scalp for several hours.

A concentration of EDTA or equivalent, sufficient to chelate at least 0.3 milligrams of calcium per milliliter of solution may be desirable since a higher concentration of chelating agent on the scalp should not inactivate as quickly as a lower concentration. A concentration sufficient to chelate 0.3 milligrams of calcium per milliliter of solution is known to be safe and not cause itching, dandruff, or other untoward problems. Higher concentrations are also acceptable for some applications.

Although the preferred composition provided in practice of this invention comprises a variety of surfactants, conditioners, preservatives, and the like, it will be apparent that the principal active ingredient is the active chelating agent for calcium ion, and such materials added to the solution to make it suitable for application to the scalp may be deleted to provide a compositon having properties somewhat different from those described. The use of conditioners and the like in the formula is considered desirable since the material is left in the hair and body, luster, et cetera, may be enhanced. In addition, it appears that the EDTA enhances these effects as compared with a "placebo" composition that is the same except for the presence of the active chelating agent.

It will also be apparent that a variety of different conditioners, surfactants, preservatives, fragrances, coloring agents and the like, may be provided in such a product. It is, therefore, to be understood that within the scope of the appended claims the invention may be practiced otherwise than as specifically described.

What is claimed is:

1. A method for reducing the rate of the average normal daily hair loss or shedding of hair by a person comprising at least daily distributing onto the scalp of the person a composition comprising ethylene diamine tetraacetic acid or salt thereof in the range of from 0.1 to 1.0 percent by weight, and leaving the chelating agent in contact with the scalp for at least eight hours.

2. The method of claim 1 wherein the ethylene diamine tetraacetic acid or salt thereof is present in a concentration of 0.2 percent by weight.

3. A method as recited in claim 1 wherein the composition comprises hair conditioners in a concentration up to 3 percent by weight, surfactant in a concentration of up to 3 percent by weight, and sufficient preservative to inhibit growth of microorganisms.

4. The method of claim 1 wherein the composition has a pH in the range of from 4 to 7.

5. The method of claim 1 wherein the composition has a pH in the range of from 5 to 5.5.

6. A method for reducing the rate of the average normal daily hair loss or shedding of hair by a person comprising at least daily distributing onto the scalp of the person a composition comprising an effective amount of active chelating agent selected from the group consisting of ethylene diamine tetraacetic acid, citric acid, and pharmaceutically acceptable soluble salts thereof sufficient to chelate at least 0.3 milligrams of divalent calcium ion per milliliter of the composition and leaving the chelating agent in contact with the scalp for at least eight hours.

7. A method for reducing the rate of the average normal daily hair loss or shedding of hair by a person comprising periodically distributing onto the scalp of the person a composition consisting essentially of ethylene diamine tetraacetic acid or salt thereof in the range of from 0.1 to 1 percent by weight, and leaving the composition in contact with the scalp of at least eight hours.

8. The method of claim 7 wherein the ethylene diamine tetraacetic acid or salt thereof is present in a concentration of 0.2 percent by weight.

9. The method fo claim 7 wherein the composition comprises hair conditioners in a concentration up to 3 percent by weight, surfactant in a concentration of up to 3 percent by weight, and sufficient preservative to inhibit growth of microorganisms.

10. The method of claim 7 wherein the composition has a pH in the range of from 4 to 7.

11. A method for reducing the rate of the average normal daily hair loss or shedding of hair by a person comprising periodically distributing onto the scalp of the person a composition consisting essentially of an active chelating agent selected from the group consisting of ethylene diamine tetraacetic acid, citric acid, and pharmaeceutically acceptable soluble salts thereof sufficient ot chelate at least 0.3 milligrams of divalent calcium per milliliter of the composition, and leaving the composition in contact with the scalp for at least eight hours.

* * * * *